United States Patent [19]

Petusky

[11] Plant 4,476

[45] Nov. 6, 1979

[54] CHRYSANTHEMUM NAMED SUNBURST SPIRIT

[75] Inventor: Kerry S. Petusky, West Chicago, Ill.

[73] Assignee: Pan-American Plant Company, West Chicago, Ill.

[21] Appl. No.: 963,884

[22] Filed: Nov. 27, 1978

[51] Int. Cl.[2] ..... A01H 5/03

[52] U.S. Cl. ..... Plt./78

[58] Field of Search ..... Plt./78

*Primary Examiner*—Robert E. Bagwill

*Attorney, Agent, or Firm*—Chas. W. Rummler

[57] ABSTRACT

A yellow chrysanthemum cultivar of the pot plant type originated as a sport of the variety "Spirit" (U.S. Plant Pat. No. 3,813) and distinguished by the light yellow coloring of its medium sized blooms. In general, this plant has the growth habit of its parent variety although the blooms are somewhat smaller in size and its response is about two to four days slower.

5 Drawing Figures

BACKGROUND OF THE NEW PLANT

This new chrysanthemum was discovered by me in May of 1977 at West Chicago, Ill., among plants of the parent variety being grown under glass for commercial exploitation, as well as for breeding purposes. This bright yellow flower, appearing on a plant normally producing only white flowers, caught my attention and because of its unusual character I reproduced it for test purposes by means of cuttings from the original stem. Subsequent propagation of this new plant through successive generations has shown its distinctive characteristics to hold true from generation to generation and to appear to be firmly fixed. Commercial scale propagation of this new plant is now being carried on at Cortez, Fla., as well as at West Chicago, Ill.

DESCRIPTION OF THE DRAWINGS

This new chrysanthemum cultivar is illustrated by the accompanying drawings, one sheet of which is a photographic view showing a potted plant of this variety in full bloom, this view having been hand painted with permanent colors to show the true coloration of the blooms, and the second sheet being a print of a machine copy of typical leaves of the new plant at several stages of maturity.

DESCRIPTION OF THE NEW PLANT

The following is a detailed description of my new chrysanthemum variety with color designations according to The R.H.S. Colour Chart published by The Royal Horticultural Society of London, England.

THE PLANT

Origin: Sport.

Parentage: "Spirit", U.S. Plant Pat. No. 3,813.

Classification:

*Botanic.*—*Chrysanthemum morifolium.*

*Commercial.*—Greenhouse pot plant.

Form: Perennial herbaceous bush.

Height: 28 to 33 cm.

Growth: Terminal, upright and vigorous, with sturdy stems of good strength.

Foliage: Quantity — abundant, with about 5 to 7 leaves on 10 cm. of stem length.

*Size of leaf.*—Length — about 6.0 to 9.9 cm. Width — about 3.4 to 5.9 cm.

*Leaf shape.*—Lobed, lanceolate and slightly serrated.

*Surface aspect.*—Canescent.

*Color.*—Upper side — 147A. Under Side — 147B.

*Venation.*—Pinnate.

*Petioles.*—Length — about 1.1 to 1.7 cm.

THE BUD

Form: Globular.

Size:

*Diameter.*—About 1.2 to 1.4 cm.

*Depth.*—About 0.8 to 1.0 cm.

Opening rate: The bud opens slowly.

Color:

*When phyllaries first divide.*—3C.

*When florets begin to unfurl.*—7A.

Phyllaries: The outside of the receptacle bears many involucral bracts which are spear-shaped and upstanding.

*Color.*—Inside — 137A. Outside — 137B.

*Surface aspect.*—Pubescent.

Peduncle: Erect and strong and about 1.0 to 1.6 cm. in length.

*Surface aspect.*—Pubescent

THE FLOWER

Flowering capability: This plant can be flowered the year around with photoperiod control.

Recommended flowering:

*Northern United States.*—March through November.

*Southern United States.*—Year around.

Natural season flowering: October 27 to November 5.

Blooms:

*Flower type.*—Composite and decorative.

*Size.*—Medium. Diameter — about 7.9 to 10.3 cm. Depth — about 1.5 to 1.8 cm.

*Borne.*—Singly when disbudded and in multiples when grown as a spray plant, each bloom comprising a head of many florets borne on a receptacle.

Shape:

*When bloom first opens.*—Cup-shaped.

*As the bloom matures.*—It tends to flatten out.

Florets: Numerous in number.

*Form.*—Decorative with tubular (spooned) ray petals.

| Color: | January | March | May |
|---|---|---|---|
| Outer florets: | | | |
| Upper side - | 4C, 5C | 5C | 5C |
| Under side - | 4C | 6D | 6D |
| Inside florets: | | | |
| Upper side - | 6A, 6B | 6B | 6A |
| Reverse side - | 7C | 7C | 7C |

*Tonality at a distance of about 2 meters.*—6B.

*Firmness.*—Medium.

*Appearance.*—Very slightly shiny.

*Discoloration.*—Very slight fade as full bloom matures.

*Persistence.*—Florets hang on and dry.

Peduncle: Upright and sturdy.

*Length.*—About 1.0 to 1.6 cm.

*Color.*—147B.

Fragrace: Typical chrysanthemum.

Lasting quality: On the plant — 3 weeks. The blooms of this plant are not recommended for cut flower use.

REPRODUCTIVE ORGANS

Stamens: Arrangement — Syngenesious. Number — 5.

*Filaments.*—About 2 to 4 mm. in length.

*Color.*—Light yellow.

*Pollen.*—Color — yellow.

Pistils: Number — 1 to each ray and disc floret.

*Styles.*—About 4 to 6 mm. in length.

*Stigma.*—Color — yellow.

Ovaries: Inferior, bicarpellate.

This new chrysanthemum cultivar is substantially like its parent insofar as its habit of growth is concerned. The new plant is distinguished from its parent by the bright yellow coloration of its flowers, which are approximately 1.2 cm. smaller in diameter than those of the parent and as far as response is concerned, the new plant is about two to four days slower than the parent.

I claim:

1. A new and distinctive cultivar of chrysanthemum pot plant, substantially as herein shown and described, particularly characterized in uniqueness, when compared with its parent "Spirit", by the bright yellow coloration of its bloooms, the somewhat smaller size of its flowers and its slower flowering response.

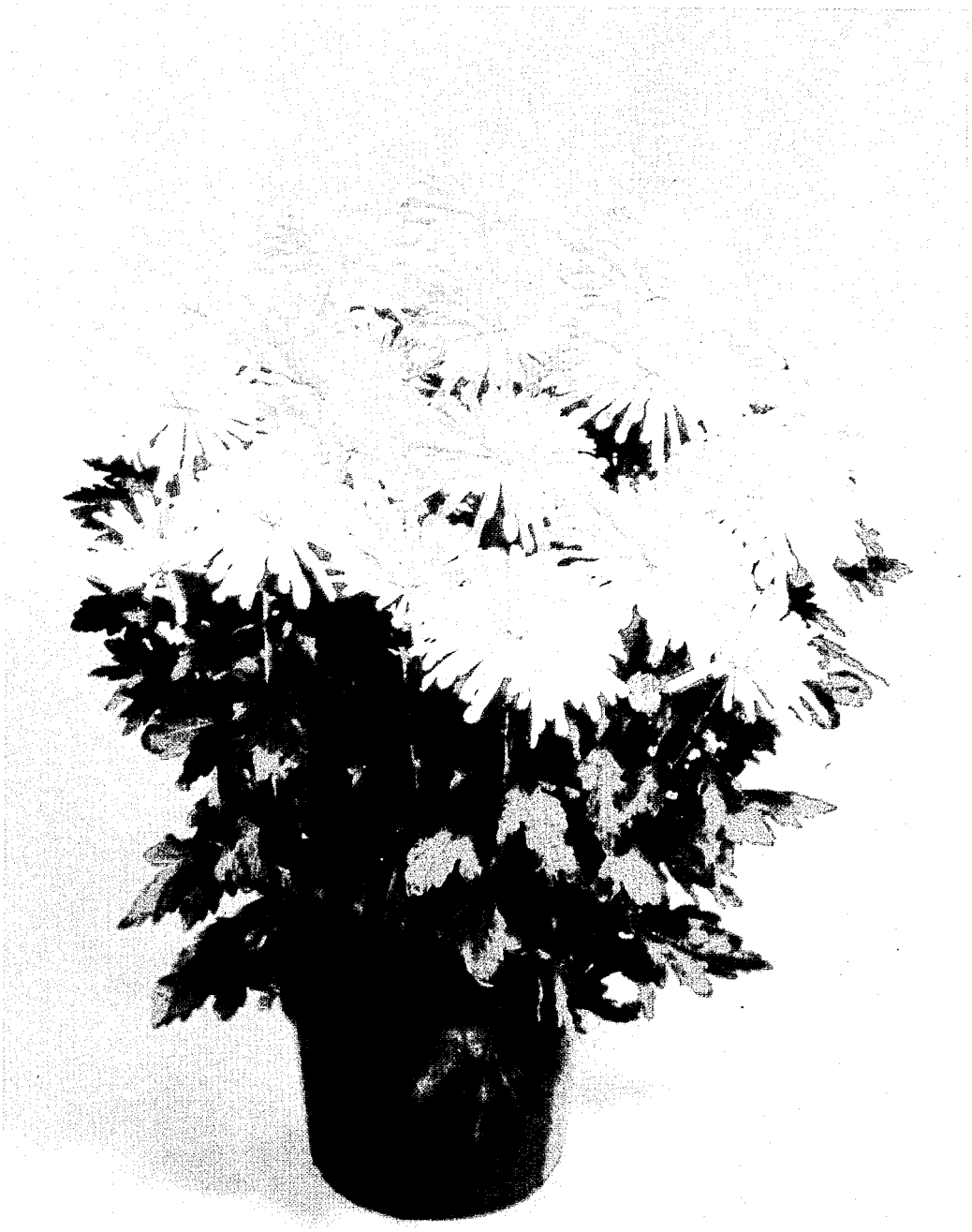

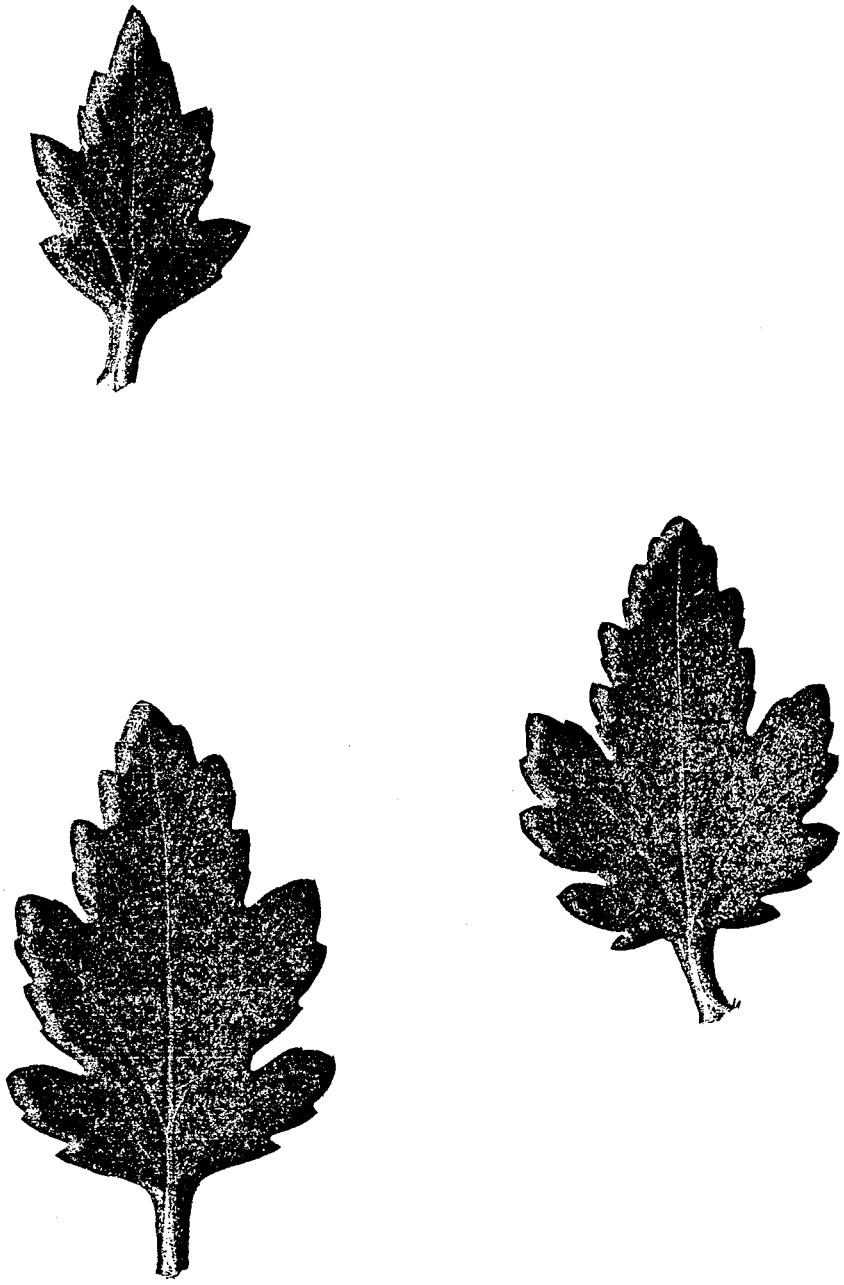

* * * * *